US012686670B2

(12) United States Patent
Kim et al.

(10) Patent No.: US 12,686,670 B2
(45) Date of Patent: Jul. 21, 2026

(54) COMPOUND, NON-AQUEOUS ELECTROLYTE SOLUTION INCLUDING THE SAME, AND LITHIUM SECONDARY BATTERY

(71) Applicants: LG Chem, Ltd., Seoul (KR); LG Energy Solution, Ltd., Seoul (KR)

(72) Inventors: Jung Keun Kim, Daejeon (KR); Su Jeong Kim, Daejeon (KR); Mi Sook Lee, Daejeon (KR); Won Kyun Lee, Daejeon (KR); Duk Hun Jang, Daejeon (KR); Jeong Ae Yoon, Daejeon (KR); Kyoung Hoon Kim, Daejeon (KR); Chul Haeng Lee, Daejeon (KR); Mi Yeon Oh, Daejeon (KR); Kil Sun Lee, Daejeon (KR); Jung Min Lee, Daejeon (KR); Esder Kang, Daejeon (KR); Chan Woo Noh, Daejeon (KR); Chul Eun Yeom, Daejeon (KR)

(73) Assignees: LG Chem, Ltd., Seoul (KR); LG Energy Solution, Ltd., Seoul (KR)

( * ) Notice: Subject to any disclaimer, the term of this patent is extended or adjusted under 35 U.S.C. 154(b) by 532 days.

(21) Appl. No.: 18/274,594

(22) PCT Filed: Mar. 23, 2022

(86) PCT No.: PCT/KR2022/004089
§ 371 (c)(1),
(2) Date: Jul. 27, 2023

(87) PCT Pub. No.: WO2022/203402
PCT Pub. Date: Sep. 29, 2022

(65) Prior Publication Data

US 2024/0109858 A1 Apr. 4, 2024

(30) Foreign Application Priority Data

| | | |
|---|---|---|
| Mar. 23, 2021 | (KR) | 10-2021-0037393 |
| Mar. 25, 2021 | (KR) | 10-2021-0039092 |
| Apr. 2, 2021 | (KR) | 10-2021-0043329 |
| Mar. 23, 2022 | (KR) | 10-2022-0035958 |

(51) Int. Cl.
*C07D 327/04* (2006.01)
*H01M 10/052* (2010.01)
*H01M 10/0567* (2010.01)

(52) U.S. Cl.
CPC ........ *C07D 327/04* (2013.01); *H01M 10/052* (2013.01); *H01M 10/0567* (2013.01)

(58) Field of Classification Search
CPC .................................................... C07D 327/04
See application file for complete search history.

(56) References Cited

U.S. PATENT DOCUMENTS

| | | | |
|---|---|---|---|
| 2013/0171514 | A1 | 7/2013 | Mio et al. |
| 2013/0337342 | A1 | 12/2013 | Hallac et al. |
| 2014/0093787 | A1 | 4/2014 | Abe et al. |
| 2017/0271715 | A1 | 9/2017 | Kim et al. |
| 2018/0248226 | A1 | 8/2018 | Kono et al. |
| 2020/0266489 | A1 | 8/2020 | Han et al. |
| 2020/0335823 | A1 | 10/2020 | Takahashi et al. |
| 2021/0313624 | A1 | 10/2021 | Morinaka et al. |

FOREIGN PATENT DOCUMENTS

| | | | |
|---|---|---|---|
| CN | 103493280 | A | 1/2014 |
| CN | 104662716 | A | 5/2015 |
| CN | 110676511 | A | 1/2020 |
| CN | 111276746 | A | 6/2020 |
| CN | 111527636 | A | 8/2020 |
| CN | 111542963 | A | 8/2020 |
| CN | 112174932 | A | 1/2021 |
| CN | 112271327 | A | 1/2021 |
| CN | 112470322 | A | 3/2021 |
| EP | 2704246 | A1 | 3/2014 |
| EP | 3726636 | A1 | 10/2020 |
| JP | 2016066481 | A | 4/2016 |
| JP | 2017045724 | A | 3/2017 |
| JP | 2017208246 | A | 11/2017 |
| KR | 20130043221 | A | 4/2013 |
| KR | 20140031233 | A | 3/2014 |
| KR | 20170108589 | A | 9/2017 |
| KR | 20180050373 | A | 5/2018 |
| KR | 20180088908 | A | 8/2018 |
| KR | 101941401 | B1 | 1/2019 |
| KR | 20200041171 | A | 4/2020 |
| KR | 20200090223 | A | 7/2020 |
| KR | 20210033040 | A | 3/2021 |

(Continued)

OTHER PUBLICATIONS

Machine translation of KR20210122480A, published on Oct. 12, 2021 (Year: 2021).*

(Continued)

*Primary Examiner* — Anca Eoff
(74) *Attorney, Agent, or Firm* — Lerner David LLP

(57) ABSTRACT

The present invention relates to a compound capable of lowering the flammability of a non-aqueous electrolyte when included in the non-aqueous electrolyte and improving the life properties of a battery by forming an electrode-electrolyte interface which is stable at high temperatures and low in resistance, and relates to a compound represented by Formula I descried herein, a non-aqueous electrolyte solution and a lithium secondary battery both including the compound,

[Formula I]

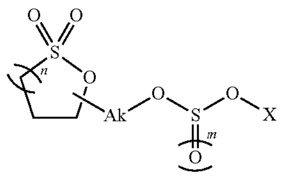

n, m, Ak, and X are described herein.

10 Claims, No Drawings

(56) References Cited

FOREIGN PATENT DOCUMENTS

| | | | | |
|---|---|---|---|---|
| KR | 20210110085 A | | 9/2021 | |
| KR | 20210122480 A | * | 10/2021 | ........ H01M 10/0567 |
| WO | 2013184881 A1 | | 12/2013 | |
| WO | 2019156434 A1 | | 8/2019 | |
| WO | 2020036222 A1 | | 2/2020 | |
| WO | 2021043175 A1 | | 3/2021 | |

OTHER PUBLICATIONS

Machine translation of KR 10-2021-0110085A, published on Sep. 7, 2021 (Year: 2021).*

International Search Report for PCT/KR2022/004089 mailed Jun. 24, 2022. 3 pages.

Extended European Search Report including Written Opinion for Application No. 22776102.0 dated Jun. 18, 2024, pp. 1-5.

* cited by examiner

COMPOUND, NON-AQUEOUS ELECTROLYTE SOLUTION INCLUDING THE SAME, AND LITHIUM SECONDARY BATTERY

CROSS-REFERENCE TO RELATED APPLICATIONS

The present application is a national stage entry under U.S.C. § 371 of International Application No. PCT/KR2022/004089 filed on Mar. 23, 2022, which claims priority from Korean Patent Applications No. 10-2021-0037393 filed on Mar. 23, 2021, 10-2021-0039092 filed on Mar. 25, 2021, 10-2021-0043329 filed on Apr. 2, 2021 and 10-2022-0035958 filed on Mar. 23, 2022, all the disclosures of which are incorporated by reference herein.

TECHNICAL FIELD

The present invention relates to a sultone-based compound, and a non-aqueous electrolyte solution and a lithium secondary battery, both including the same.

BACKGROUND ART

Recently, as the application area of lithium secondary batteries has rapidly expanded to the power supply of electronic devices such as electricity, electronics, communications, and computers, as well as the power storage supply of large-area devices such as automobiles and power storage devices, the demand for high-capacity, high-output, and high-stability secondary batteries is increasing.

Lithium secondary batteries are generally manufactured by applying a positive electrode active material made of a lithium-containing transition metal oxide and the like, and a carbon-material or silicon-material negative electrode active material capable of occluding and releasing lithium ions, and selectively a material in which a binder and a conductive material are mixed, on a positive electrode current collector and a negative electrode current collector, respectively, to manufacture a positive electrode and a negative electrode, and laminate the positive electrode and the negative electrode on each side of a separator to form an electrode assembly of a predetermined shape, and then inserting the electrode assembly and a non-aqueous electrolyte solution into a battery case. Here, in order to secure the performance of the battery, formation and aging processes are almost essentially performed.

The formation process is a step of activating the secondary battery by repeating charging and discharging after the battery assembly, and during the charging, lithium ions released from the lithium-containing transition metal oxide used as the positive electrode are transferred to and inserted into the carbon-material negative active material used as the negative electrode. At this time, highly reactive lithium ions are reacted with an electrolyte to generate compounds such as $Li_2CO_3$, $Li_2O$, and LiOH, and these compounds form a solid electrolyte interface (SEI) layer on the surface of an electrode. Since the SEI layer greatly affects the lifespan and capacity retention, SEI layer formation is an important factor.

Recently, for lithium secondary batteries for vehicles in particular, high-capacity, high-power, and long-lifespan properties are becoming important. In order to achieve high capacity, as for a positive electrode, a positive electrode active material which is high in energy density but low in stability is used, and accordingly, it is necessary to form an active material-electrolyte interface capable of stabilizing the positive electrode active material by protecting the surface of the positive electrode active material. As for a negative electrode, problems such as surface species of the negative electrode being decomposed in an electrolyte solution and causing side reactions have been reported, so that an SEI layer needs to be formed low in resistance while being robust. In addition, since an SEI layer may slowly collapse when stored at high temperatures and cause problems such as electrode exposure, there have been attempts to develop an additive in an electrolyte solution which helps to generate an SEI interface capable of suppressing side reactions during high-temperature storage. Meanwhile, 1,3-propane sultone, which is an additive known to be effective in forming an SEI layer of a negative electrode, has toxicity issues, and 1,3,2-dioxathiolane 2,2-dioxide and the like has problems such as gas generation, chemical stability, and the like.

As described above, as high-temperature driving and long-term lifespan properties have become important for lithium secondary batteries, an electrolyte decomposition reaction caused by an oxidation-reduction reaction occurring at an interface between an electrolyte and an electrode during repeated cycles is accumulated, and due to resistance increased thereby, there is a problem in that the lifespan properties are deteriorated.

DISCLOSURE OF THE INVENTION

Technical Problem

An aspect of the present invention provides a compound, when included in a non-aqueous electrolyte, capable of lowering the flammability of a non-aqueous electrolyte solution, and allowing a thin and stable SEI layer to be formed, thereby implementing a lithium secondary battery with excellent high-temperature stability and lifespan properties, and a non-aqueous electrolyte solution and a lithium secondary battery both including the non-aqueous electrolyte solution.

Technical Solution

According to an aspect of the present invention, there are provided a compound, a non-aqueous electrolyte solution, and a lithium secondary battery.

(1) The present invention provides a compound represented by Formula I below.

[Formula I]

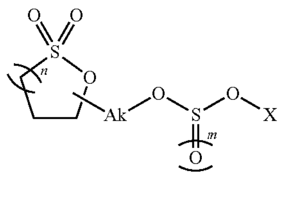

In Formula I above, n and m are each independently 1 or 2, Ak is a substituted or unsubstituted $C_1$-$C_{10}$ alkylene group, and X is a $C_1$-$C_{10}$ alkyl group substituted with one or more halogen elements; a —Y1-C≡C—Y2 group; or a —Y1-CN group, wherein the Y1 is a direct linkage, or a substituted or unsubstituted $C_1$-$C_{10}$ alkylene group, and the Y2 is hydrogen, or a substituted or unsubstituted $C_1$-$C_{10}$ alkyl group.

(2) In (1) above, the present invention provides a compound in which the compound represented by Formula I above is a compound represented by Formula 1 below.

[Formula 1]

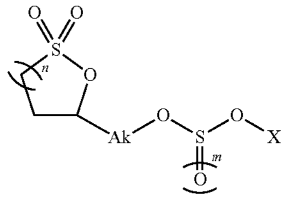

In Formula 1 above, n and m are each independently 1 or 2, Ak is a substituted or unsubstituted $C_1$-$C_{10}$ alkylene group, and X is a $C_1$-$C_{10}$ alkyl group substituted with one or more halogen elements, a —Y1-C≡C—Y2 group, or a —Y1-CN group, wherein the Y1 is a direct linkage, or a substituted or unsubstituted $C_1$-$C_{10}$ alkylene group, and the Y2 is hydrogen, or a substituted or unsubstituted $C_1$-$C_{10}$ alkyl group.

(3) In (1) or (2) above, the present invention provides a compound in which the Ak is an unsubstituted $C_1$-$C_6$ alkylene group.

(4) In any one of (1) to (3) above, the present invention provides a compound in which the X is a $C_1$-$C_6$ alkyl group substituted with one or more halogen elements.

(5) In any one of (1) to (3) above, the present invention provides a compound in which the X is a —Y1'—C≡C—Y2' group, wherein the Y1' is an unsubstituted $C_1$-$C_6$ alkylene group, and the Y2' is hydrogen, or an unsubstituted $C_1$-$C_6$ alkyl group.

(6) In any one of (1) to (3) above, the present invention provides a compound in which the X is a —Y1'—CN group, wherein the Y1' is an unsubstituted $C_1$-$C_6$ alkylene group.

(7) In any one of (1) to (3) above, the present invention provides a compound in which the compound represented by Formula I above is a compound which is any one among compounds represented by Formula a to Formula f below.

[Formula a]

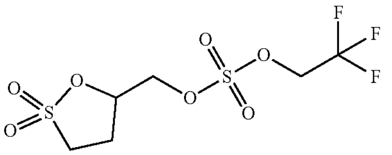

[Formula b]

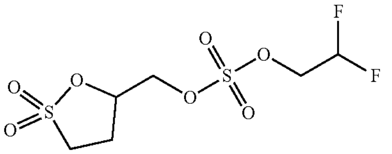

[Formula c]

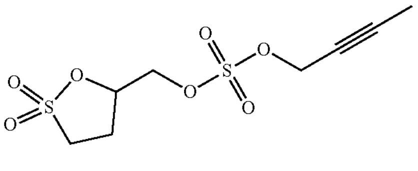

-continued

[Formula d]

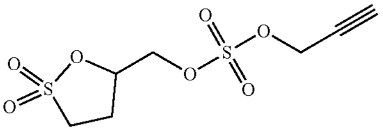

[Formula e]

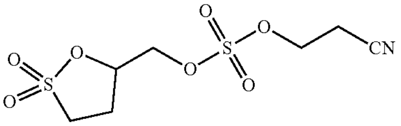

[Formula f]

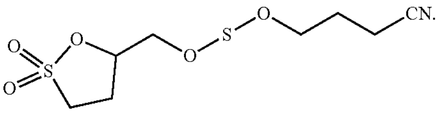

(8) In addition, the present invention provides a non-aqueous electrolyte solution including an organic solvent, a lithium salt, and the compound according to any one of (1) to (7) above.

(9) In (8) above, the present invention provides a non-aqueous electrolyte solution in which the compound is included in an amount of 0.01 wt % to 10 wt % based on the total weight of the non-aqueous electrolyte.

(10) In addition, the present invention provides a lithium secondary battery including the non-aqueous electrolyte solution according to (8) or (9) above.

Advantageous Effects

When a compound represented by Formula I and according to the present invention is included in a non-aqueous electrolyte solution, the flammability of the non-aqueous electrolyte solution may be lowered, and a thin and stable SEI layer may be formed, so that a lithium secondary battery with excellent high-temperature stability and lifespan properties may be provided.

BEST MODE FOR CARRYING OUT THE INVENTION

Hereinafter, the present invention will be described in more detail.

It will be understood that terms or words used in the present specification and claims shall not be construed as being limited to having meanings defined in commonly used dictionaries, but should be interpreted as having meanings and concepts consistent with the technical idea of the present invention based on the principle that an inventor may appropriately define concepts of the terms to best explain the invention.

The terms used in the present invention are only used to describe specific embodiments, and are not intended to limit the present invention. Singular expressions include plural expressions unless the context clearly indicates otherwise.

It should be understood that the term 'comprise,' or 'have' is intended to specify the presence of stated features, integers, steps, operations, elements, parts, or combinations thereof in the disclosure, but do not preclude the presence or addition of one or more other features, integers, steps, operations, elements, parts, or combinations thereof.

In the present invention, in the description of '$C_a$ to $C_b$,' 'a' and 'b' means the number of carbon atoms. For example, a '$C_1$ to $C_{10}$ alkylene group' refers to an alkylene group including 1 to 10 carbon atoms, that is, $—CH_2—$, $—CH_2CH_2—$, $—CH_2CH_2CH_2—$, $—CH_2CH(CH_3)—$, $—CH(CH_3)\ CH_2—$, $—CH(CH_3)\ CH_2CH_2—$, and the like.

The present inventors have repeatedly conducted research to develop a lithium secondary battery with excellent performance at high temperatures, and have found that when a sultone-based compound represented by Formula 1 below is used as a non-aqueous electrolyte solution additive, high-temperature storage properties and lifespan properties are improved, and have completed the present invention.

Compound Represented by Formula I

The present invention provides a compound represented by Formula I below.

[Formula I]

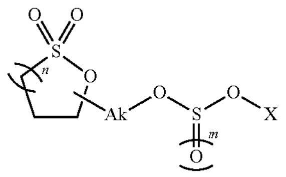

In Formula I above, n and m are each independently 1 or 2, Ak is a substituted or unsubstituted $C_1$-$C_{10}$ alkylene group, and X is a $C_1$-$C_{10}$ alkyl group substituted with one or more halogen elements, a —Y1-C≡C—Y2 group, or a —Y1-CN group, wherein the Y1 is a direct linkage, or a substituted or unsubstituted $C_1$-$C_{10}$ alkylene group, and the Y2 is hydrogen, or a substituted or unsubstituted $C_1$-$C_{10}$ alkyl group.

In the present invention, a substituent in the substituted alkylene group or substituted alkyl group may be one or more substituents selected from deuterium, a halogen group, a hydroxy group, an amino group, a thiol group, a nitro group, a nitrile group, a silyl group, or a straight or branched $C_1$-$C_6$ alkoxy group.

1,3-propane sultone (PS) typically used as an electrolyte solution additive is limited in use due to the toxicity thereof, but the compound represented by Formula I of the present invention is low in toxicity compared to 1,3-propane sultone, and includes, as a terminal group, a functional group for withdrawing electrons, and includes a sulfite group or sulfate group, and thus, may form a film, which is durable and has high lithium salt conductivity, on the surface of a positive electrode and a negative electrode.

The compound represented by Formula I above has an electron withdrawing group positioned at a terminal (position X), thereby lowering the lowest unoccupied molecular orbital (LUMO) energy to increase reducibility. Therefore, a film (SEI layer) may be more easily formed on the surface of an electrode.

In addition, the compound represented by Formula I above contains a sultone group with a high ion conductivity in the molecule, thereby minimizing the increase in interface resistance, while forming a stable film capable of preventing an electrode surface from being exposed so as to prevent side reactions between an electrode and an electrolyte, to suppress $O_2$ generation, and to effectively control transition metal elution from a positive electrode.

As a result, a lithium secondary battery having improved high-temperature storage properties and high-temperature cycle properties may be implemented.

A sultone-based compound represented by Formula I of the present invention may be prepared by sulfonating a diol-containing alkene compound or a diol-containing halogen compound; preparing a hydroxyl group-containing sultone compound through condensation of one alcohol group in the diol and a sulfonate group; preparing a compound containing a chlorosulfite group through a sulfonation reaction with a residual hydroxyl group; preparing a sulfite group-containing compound by reacting the chlorosulfite group-containing compound with an alcohol group; and preparing a sulfate group-containing compound by oxidizing the sulfite group, but is not limited thereto, and may be prepared by a known method.

Meanwhile, the compound represented by Formula I has a reduction potential higher than that of a non-aqueous solvent, and thus may be decomposed first under cell driving conditions to form a robust film, and the reduction potential may be measured in the following manner using a Gaussian 09 program package (Gaussian 09 Revision C.01, Gaussian Inc., Wallingford, C T, 2009) to which a DFT calculation method is applied.

1) Calculate the stable structural energy ($E_{neut}$) of the compound in the state before it is reduced, and the stable structural energy ($E_{red}$) of the compound in the reduced state. 2) Define $E_{neut}$–$E_{red}$–1.45 eV as a reduction stability value. At this time, the structural stabilization calculation is performed in the state in which the polarizable continuum model (PCM) method is applied.

According to the present invention, in Formula I above, Ak may be an unsubstituted $C_1$-$C_6$ alkylene group, and more specifically, an unsubstituted $C_1$-$C_5$ alkylene group. In this case, the synthesis of the compound is facilitated, and when used as an additive for a non-aqueous electrolyte solution, the resistance of an SEI layer may be prevented from increasing, and consequently, the resistance of a battery may be prevented from increasing.

According to the present invention, in Formula I above, X may be a $C_1$-$C_6$ alkyl group substituted with one or more halogen elements, and more specifically, a $C_1$-$C_5$ alkyl group substituted with one or more halogen elements. In this case, electron-withdrawing force is stronger, resulting in high reducibility, so that an SEI layer may be more easily formed on the surface of an electrode. Meanwhile, the halogen element may specifically be a fluorine element.

According to the present invention, in Formula I above, X is a —Y1'—C≡C—Y2' group, wherein the Y1' may be an unsubstituted $C_1$-$C_6$ alkylene group, and the Y2' may be hydrogen, or an unsubstituted $C_1$-$C_6$ alkyl group. In this case, a C≡C triple bond in one molecule is polymerized with a C≡C triple bond in another molecule, so that a more robust SEI layer may be formed. The Y1' may specifically be an unsubstituted $C_1$-$C_5$ alkylene group, and the Y2' may be hydrogen, or an unsubstituted $C_1$-$C_5$ alkyl group.

According to the present invention, in Formula I above, X is a —Y1'—CN group, wherein the Y1' may be an unsubstituted $C_1$-$C_6$ alkylene group. The Y1' may specifically be an unsubstituted $C_1$-$C_5$ alkylene group. In this case, electron-withdrawing force is stronger, resulting in high reducibility, so that an SEI layer may be more easily formed on the surface of an electrode.

According to the present invention, the compound represented by Formula I above may be a compound represented by Formula 1 below.

[Formula 1]

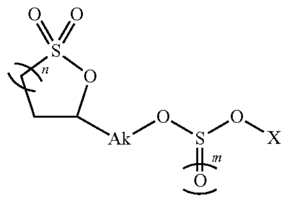

In Formula 1 above, n and m are each independently 1 or 2, Ak is a substituted or unsubstituted $C_1$-$C_{10}$ alkylene group, and X is a $C_1$-$C_{10}$ alkyl group substituted with one or more halogen elements, a —Y1-C≡C—Y2 group, or a —Y1-CN group, wherein the Y1 is a direct linkage, or a substituted or unsubstituted $C_1$-$C_{10}$ alkylene group, and the Y2 is hydrogen, or a substituted or unsubstituted $C_1$-$C_{10}$ alkyl group.

When a compound such as 1,3-propane sultone or 1,4-butane sultone is used as an electrolyte additive, there is a problem in that a ring opening reaction occurs and toxicity is expressed. However, when a compound in which a -Ak-O—(S═O)$_m$OX group is substituted at a position next to oxygen in a ring structure as shown in Formula 1 above is used as an electrolyte additive, it is possible to prevent the ring opening reaction, the ring opening reaction may be prevented, so that the toxicity may be prevented from being expressed.

In Formula 1 above, the n, m, Ak, X, Y1, and Y2 may be the same as the n, m, Ak, X, Y1, and Y2 of Formula I above.

In Formula 1 above, Ak may specifically be an unsubstituted $C_1$-$C_6$ alkylene group, and X may be a $C_1$-$C_6$ alkyl group substituted with one or more halogen elements; a —Y1'—C≡C—Y2' group (wherein the Y1' is an unsubstituted $C_1$-$C_6$ alkylene group, and the Y2' is hydrogen; or an unsubstituted $C_1$-$C_6$ alkyl group); or a —Y1'—CN group (wherein the Y1' is an unsubstituted $C_1$-$C_6$ alkylene group).

According to the present invention, the compound represented by Formula I above may be a compound represented by any one of Formula a to Formula f below.

[Formula a]

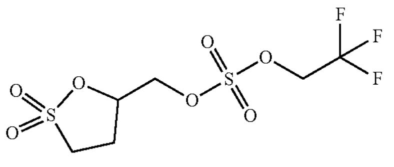

[Formula b]

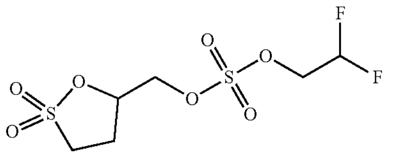

[Formula c]

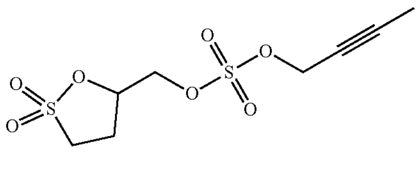

-continued

[Formula d]

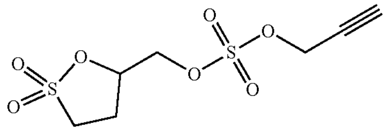

[Formula e]

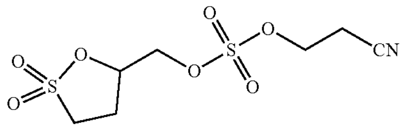

[Formula f]

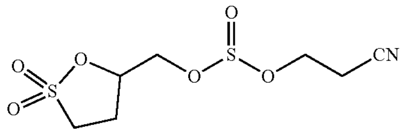

Non-Aqueous Electrolyte Solution

The present invention provides a non-aqueous electrolyte solution including an organic solvent, a lithium salt, and a compound represented by Formula I above.

(1) Compound Represented by Formula I

The non-aqueous electrolyte solution according to the present invention includes a compound represented by Formula I above as an additive.

When a compound represented by Formula I above, which may reduce toxicity issues, is included in the non-aqueous electrolyte solution, a thin and stable SEI layer may be formed, so that a lithium secondary battery with excellent high-temperature stability and lifespan properties may be provided.

According to the present invention, the compound may be included in an amount of 0.01 wt % to 10 wt %, specifically 0.01 wt % to 5 wt %, 0.01 wt % to 1 wt %, or 0.1 wt % to 1 wt % based on the total weight of the non-aqueous electrolyte solution. In this case, when the non-aqueous electrolyte solution is applied to a secondary battery, a robust SEI layer may be formed to contribute to improving long-term lifespan properties and reducing gas generation.

(2) Organic Solvent

The organic solvent is a non-aqueous solvent commonly used in a lithium secondary battery, and is not limited as long as it can minimize decomposition caused by an oxidation reaction and the like during charging and discharging of a secondary battery, and can exhibit desired properties when used together with an additive.

The organic solvent may be, for example, a linear carbonate or cyclic carbonate, a linear or cyclic ester, ester, glyme, nitrile (acetonitrile, SN, etc.), and the like, but is not limited thereto. As the organic solvent, a carbonate-based electrolyte solution solvent including a cyclic carbonate, a linear carbonate, or a carbonate compound, which is a mixture thereof, may be representatively used.

Meanwhile, specific examples of the cyclic carbonate compound may include ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), but are not limited thereto.

Specific examples of the linear carbonate compound may include dimethyl carbonate (DMC), diethyl carbonate (DEC), dipropyl carbonate, ethyl methyl carbonate (EMC), methyl propyl carbonate, ethyl propyl carbonate, and the like, but are not limited thereto.

Specific examples of the linear ester compound may include methyl acetate, ethyl acetate, propyl acetate, methyl propionate, ethyl propionate, propyl propionate, butyl propionate, and the like, but are not limited thereto.

Specific examples of the cyclic ester compound may include γ-butyrolactone, γ-valerolactone, γ-caprolactone, σ-valerolactone, ε-caprolactone, and the like, but are not limited thereto.

Specific examples of the ether-based solvent may include dimethyl ether, diethyl ether, dipropyl ether, methylethyl ether, methylpropyl ether, ethylpropyl ether, 1,3-dioxolane (DOL), 2,2-bis(trifluoromethyl)-1,3-dioxolane (TFDOL), and the like, but are not limited thereto.

The glyme-based solvent, which is a solvent having a higher dielectric constant and lower surface tension than those of a linear carbonate-based organic solvent, and having less reactivity with a metal, may include dimethoxyethane (glyme, DME), diethoxyethane, digylme, tri-glyme, tetra-glyme (TEGDME), and the like, but is not limited thereto.

Specific examples of the nitrile-based solvent may include acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, 4-fluorophenylacetonitrile, and the like, but are not limited thereto.

Meanwhile, ethylene carbonate and propylene carbonate, which are cyclic carbonate-based organic solvents, may be preferably used since they are high-viscosity organic solvents with high dielectric constants, and thus are capable of well dissociating a lithium salt in an electrolyte solution. Such a cyclic carbonate may be further preferably used when mixed with a low-viscosity, low-dielectric constant linear carbonate, such as dimethyl carbonate, diethyl carbonate, and ethylmethyl carbonate, in an appropriate ratio and used since an electrolyte solution with high electrical conductivity may be prepared. In this case, the cyclic carbonate and the linear carbonate may be mixed in a volume ratio of 2:8 to 4:6 and used.

(3) Lithium Salt

The lithium salt is used as an electrolyte salt in a lithium secondary battery, and is used as a medium for transferring ions. Commonly, a lithium salt may include one or more compounds selected from $LiPF_6$, $LiBF_4$, $LiSbF_6$, $LiAsF_6$, $LiClO_4$, $LiN(C_2F_5SO_2)_2$, $LiN(CF_3SO_2)_2$, $CF_3SO_3Li$, $LiC(CF_3SO_2)_3$, $LiC_4BOs$, LiTFSI, LiFSI, or $LiClO_4$, and preferably, may include $LiPF_6$, but is not limited thereto. Meanwhile, as the lithium salt, one thereof, or if necessary, two or more thereof may be mixed and used.

According to the present invention, the lithium salt may be included at a concentration of 0.5 M to 5 M, and preferably, may be included at a concentration of 0.5 M to 4 M. When the concentration of a lithium salt is within the above range, the concentration of lithium ions in the electrolyte solution is suitable, so that the charging and discharging of a battery may be properly performed, and since the viscosity of the electrolyte solution is suitable, the wetting in the battery is excellent, so that the battery performance may be improved.

(4) Other Electrolyte Additives

The non-aqueous electrolyte solution may further include other electrolyte additives.

The other electrolyte additives are electrolyte additives known in the art which may additionally added to the non-aqueous electrolyte solution of the present invention, and may be, for example, vinylene carbonate, vinyl ethylene carbonate, catechol carbonate, α-bromo-γ-butyrolactone, methyl chloroformate, succinimide, N-benzyloxycarbonyloxysuccinimide, N-hydroxysuccinimide, N-chlorosuccinimide, methyl cinnamate, 1,3,5-tricyanobenzene, tetracyanoquinodimethane, pyrocarbonate, cyclohexylbenzene, propane sultone, succinonitrile, adiponitrile, ethylene sulfate, propene sultone, fluoroethylene carbonate, $LiPO_2F_2$, lithium difluorooxalatoborate (LiODFB), lithium bis-(oxalato)borate (LiBOB), 3-trimethoxysilanyl-propyl-N-aniline (TMSPa), tris(trimethylsilyl)phosphite (TMSPi), 12-crown-4, 15-crown-5, 18-crown-6, aza-ethers, boranes, borates, boronates, ferrocene and a derivative thereof, $LiBF_4$, and the like.

The other electrolyte additives may be included in an amount of 0.01 wt % to 10 wt %, preferably 0.05 wt % to 7.0 wt %, and more preferably 0.05 wt % to 5.0 wt %.

Lithium Secondary Battery

The present invention provides a lithium secondary battery including the non-aqueous electrolyte solution.

Specifically, the lithium secondary battery includes a positive electrode including a positive electrode active material, a negative electrode including a negative electrode active material, a separator interposed between the positive electrode and the negative electrode, and the non-aqueous electrolyte solution according to the present invention.

At this time, the lithium secondary battery of the present invention may be manufactured by a common method known in the art. For example, the lithium secondary battery of the present invention may be manufactured by forming an electrode assembly in which a separator is interposed between a positive electrode and a negative electrode, followed by inserting the electrode assembly into a battery case, and then injecting the non-aqueous electrolyte solution according to the present invention thereto.

(1) Positive Electrode

The positive electrode may be manufactured by coating a positive electrode slurry, which includes a positive electrode active material, a binder, a conductive material, a solvent, etc., on a positive electrode current collector.

The positive electrode current collector is not particularly limited as long as it has conductivity without causing a chemical change in the battery. For example, stainless steel, aluminum, nickel, titanium, fired carbon, or aluminum or stainless steel that is surface-treated with one of carbon, nickel, titanium, silver, etc., may be used. Also, microscopic irregularities may be formed on the surface of the positive electrode current collector to improve the coupling force of a positive electrode active material, and the positive electrode current collector may be used in various forms, such as a film, a sheet, a foil, a net, a porous body, a foam body, and a non-woven fabric body.

The positive electrode active material is a compound capable of reversible intercalation and de-intercalation of lithium, and specifically, may include a lithium metal oxide including one or more metals, such as cobalt, manganese, nickel, and aluminum, and lithium. More specifically, the lithium metal oxide may be a lithium-manganese-based oxide (e.g., $LiMnO_2$, $LiMn_2O_4$, etc.), a lithium-cobalt-based oxide (e.g., $LiCoO_2$, etc.), a lithium-nickel-based oxide (e.g., $LiNiO_2$, etc.), a lithium-nickel-manganese-based oxide (e.g., $LiNi_{1-Y}Mn_YO_2$ (wherein $0<Y<1$), $LiMn_{2-Z}Ni_ZO_4$ (wherein $0<Z<2$), etc.), a lithium-nickel-cobalt-based oxide (e.g., $LiNi_{1-Y1}Co_{Y1}O_2$ (wherein $0<Y1<1$), etc.), a lithium-manganese-cobalt-based oxide (e.g., $LiCo_{1-Y2}Mn_{Y2}O_2$ (wherein $0<Y2<1$), $LiMn_{2-z1}Co_{z1}O_4$ (wherein $0<Z1<2$, etc.), a lithium-nickel-manganese-cobalt-based oxide (e.g., $Li(Ni_pCO_qMn_{r1})O_2$ (wherein $0<p<1$, $0<q<1$, $0<r1<1$, p+q+ r1=1) or $Li(Ni_{p1}Co_{q1}Mn_{r2})O_4$ (wherein $0<p1<2$, $0<q1<2$, $0<r2<2$, $p1+q1+r2=2$, etc.), or a lithium-nickel-cobalt-transition metal (M) oxide (e.g., $Li(Ni_{p2}Co_{q2}Mn_{r3}A_{S2})O_2$ (wherein A is selected from the group consisting of Al, Fe, V, Cr, Ti, Ta, Mg, and Mo, and p2, q2, r3, and s2 are each an atomic fraction of stand-alone elements, wherein $0<p2<1$, $0<q2<1$, $0<r3<1$, $0<s2<1$, $p2+q2+r3+s2=1$, etc.) and the like, and any one thereof or a compound of two or more thereof may be included.

Among these, due to the fact that the capacity properties and stability of a battery may be increased, the lithium metal oxide may be $LiCoO_2$, $LiMnO_2$, $LiNiO_2$, a lithium nickel-manganese-cobalt oxide (e.g., $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, $Li(Ni_{0.8}Mn_{0.1}Co_{0.1})O_2$, etc.), or a lithium-nickel-cobalt-aluminum oxide (e.g., $Li(Ni_{0.8}Co_{0.15}Al_{0.05})O_2$, etc.). When considering the effect of remarkable improvement according to the type and content ratio control of constituent elements forming a lithium metal oxide, the lithium metal oxide may be $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, $Li(Ni_{0.8}Mn_{0.1}Co_{0.1})O_2$, and the like, and any one thereof or a mixture of two or more thereof may be used.

The positive electrode active material may be included in an amount of 60 wt % to 99 wt %, preferably 70 wt % to 99 wt %, and more preferably 80 wt % to 98 wt % based on the total weight of solids excluding the solvent in the positive electrode slurry.

The binder is a component for assisting in coupling between an active material, a conductive material, etc., and coupling to a current collector.

Examples of the binder may include polyvinylidene fluoride, polyvinyl alcohol, carboxymethyl cellulose (CMC), starch, hydroxypropyl cellulose, regenerated cellulose, polyvinylpyrrolidone, tetrafluoroethylene, polyethylene (PE), polypropylene, an ethylene-propylene-diene monomer, a sulfonated ethylene-propylene-diene monomer, styrene-butadiene rubber, fluorine rubber, various copolymers thereof, and the like.

Commonly, the binder may be included in an amount of 1 wt % to 20 wt %, preferably 1 wt % to 15 wt %, and more preferably 1 wt % to 10 wt % based on the total weight of solids excluding the solvent in the positive electrode slurry.

The conductive material is a component for further improving the conductivity of a positive electrode active material.

The conductive material is not particularly limited as long as it has conductivity without causing a chemical change in the battery. For example, graphite; a carbon-based material such as carbon black, acetylene black, Ketjen black, channel black, furnace black, lamp black, and thermal black; conductive fiber such as carbon fiber and metal fiber; metal powder such as fluorocarbon powder, aluminum powder, and nickel powder; a conductive whisker such as zinc oxide and potassium titanate; a conductive metal oxide such as titanium oxide; and a conductive material such as a polyphenylene derivative, and the like may be used.

Commonly, the conductive material may be included in an amount of 1 wt % to 20 wt %, preferably 1 wt % to 15 wt %, and more preferably 1 wt % to 10 wt % based on the total weight of solids excluding the solvent in the positive electrode slurry.

The solvent may include an organic solvent such as N-methyl-2-pyrrolidone (NMP), and may be used in an amount such that a preferred viscosity is achieved when the positive electrode active material, and selectively a binder, a conductive material, and the like are included. For example, the solvent may be included in an amount such that the concentration of solids including the positive electrode active material, and selectively the binder and the conductive material is 50 wt % to 95 wt %, preferably 70 wt % to 95 wt %, and more preferably 70 wt % to 90 wt %.

(2) Negative Electrode

The negative electrode may be manufactured by, for example, coating a negative electrode slurry, which includes a negative electrode active material, a binder, a conductive material, a solvent, etc., on a negative electrode current collector, or a graphite electrode made of carbon (C) or a metal itself may be used as the negative electrode.

For example, when the negative electrode is manufactured by coating a negative electrode slurry on a negative electrode current collector, the negative electrode current collector typically has a thickness of 3 to 500 μm. The negative electrode current collector is not particularly limited as long as it has high conductivity without causing a chemical change in the battery. For example, copper, stainless steel, aluminum, nickel, titanium, fired carbon, or copper or stainless steel that is surface-treated with one of carbon, nickel, titanium, silver, etc., an aluminum-cadmium alloy, and the like may be used. Also, as in the case of the positive electrode current collector, microscopic irregularities may be formed on the surface of the negative electrode current collector to improve the coupling force of a negative electrode active material, and the negative electrode current collector may be used in various forms, such as a film, a sheet, a foil, a net, a porous body, a foam body, and a non-woven fabric body.

Examples of the negative electrode active material may include one or two or more kinds of negative electrode active materials selected from the group consisting of natural graphite, artificial graphite, a carbonaceous material; a metal (Me) such as a lithium-containing titanium composite oxide (LTO), Si, $SiO_x$, Sn, Li, Zn, Mg, Cd, Ce, Ni or Fe; an alloy composed of the metal (Me); an oxide ($MeO_x$) of the metal (Me); and a composite of the metal (Me) and carbon. Specifically, as the negative electrode active material, a silicon-based negative electrode active material including silicon (Si), a silicon oxide ($SiO_x$), a silicon alloy, or the like may be used. In this case, a thin and stable SEI layer including a siloxane bond may be formed, so that the high-temperature stability and lifespan properties of a battery may be further improved.

The negative electrode active material may be included in an amount of 60 wt % to 99 wt %, preferably 70 wt % to 99 wt %, and more preferably 80 wt % to 98 wt % based on the total weight of solids excluding the solvent in the negative electrode slurry.

The binder is a component for assisting in coupling between a conductive material, an active material, and a current collector. Examples of the binder may include polyvinylidene fluoride (PVDF), polyvinyl alcohol, carboxymethyl cellulose (CMC), starch, hydroxypropyl cellulose, regenerated cellulose, polyvinylpyrrolidone, tetrafluoroethylene, polyethylene, polypropylene, an ethylene-propylene-diene monomer, a sulfonated ethylene-propylene-diene monomer, styrene-butadiene rubber, fluorine rubber, various copolymers thereof, and the like.

Commonly, the binder may be included in an amount of 1 wt % to 20 wt %, preferably 1 wt % to 15 wt %, and more preferably 1 wt % to 10 wt % based on the total weight of solids excluding the solvent in the negative electrode slurry.

The conductive material is a component for further improving the conductivity of a negative electrode active material. The conductive material is not particularly limited as long as it has conductivity without causing a chemical change in the battery. For example, graphite such as natural graphite or artificial graphite; carbon black such as acetylene black, Ketjen black, channel black, furnace black, lamp black, and thermal black; conductive fiber such as carbon fiber and metal fiber; metal powder such as fluorocarbon powder, aluminum powder, and nickel powder; a conductive whisker such as zinc oxide and potassium titanate; a conductive metal oxide such as titanium oxide; or a conductive material such as a polyphenylene derivative, and the like may be used.

The conductive material may be included in an amount of 1 wt % to 20 wt %, preferably 1 wt % to 15 wt %, and more preferably 1 wt % to 10 wt % based on the total weight of solids excluding the solvent in the negative electrode slurry.

The solvent may include water, or an organic solvent such as N-methyl-2-pyrrolidone (NMP), and may be used in an amount such that a preferred viscosity is achieved when the negative electrode active material, and selectively a binder, a conductive material, and the like are included. For example, the solvent may be included in an amount such that the concentration of solids including the negative electrode active material, and selectively the binder and the conductive material is 50 wt % to 95 wt %, preferably 70 wt % to 90 wt %.

When a metal itself is used as the negative electrode, a metal thin film itself may be used as the negative electrode, or the negative electrode may be manufactured by physically bonding, roll-pressing, or depositing the metal on the negative electrode current collector. The depositing method may be electrical vapor deposition or chemical vapor deposition.

For example, the metal thin film itself, or the metal bonded/roll-pressed/deposited on the negative electrode current collector may be one metal selected from the group consisting of lithium (Li), nickel (Ni), tin (Sn), copper (Cu), and indium (In), or an alloy of two metals thereof.

(3) Separator

In addition, as the separator, a common porous polymer film typically used as a separator, for example, a porous polymer film made of a polyolefin-based polymer, such as an ethylene homocopolymer, a propylene homocopolymer, an ethylene/butene copolymer, an ethylene/hexene copolymer, and an ethylene/methacrylate copolymer may be used alone, or a laminate thereof may be used. Alternatively, a common porous non-woven fabric, for example, a non-woven fabric made of glass fiber having a high melting point or polyethylene terephthalate fiber may be used, but the present invention is not limited thereto. Also, a coated separator including a ceramic component or a polymer material may be used to secure heat resistance or mechanical strength, and selectively, may be used in a single-layered or a multi-layered structure.

The external shape of the lithium secondary battery of the present invention is not particularly limited, but may be a cylindrical shape using a can, a square shape, a pouch shape, a coin shape, or the like.

According to the present invention, there may be provided a battery module including the lithium secondary battery as a unit cell, and a battery pack including the battery module. The battery module and the battery pack include the lithium secondary battery having high capacity, high rate properties, and cycle properties, and thus may be used as a power source of a medium-and-large sized device selected from the group consisting of an electric vehicle, a hybrid electric vehicle, a plug-in hybrid electric vehicle, and a power storage system.

MODE FOR CARRYING OUT THE INVENTION

Hereinafter, the present invention will be described in more detail with reference to specific examples. However, the following examples are for illustrative purposes only to facilitate the understanding of the present invention, and do not limit the scope of the present invention. It will be apparent to those skilled in the art that various changes and modifications can be made without departing from the scope and spirit of the invention, and it is obvious that such variations and modifications are within the scope of the appended claims.

SYNTHESIS EXAMPLES

Synthesis Example 1. Preparation of Compound Represented by Formula a

After a round-bottom flask was placed in an ice bath, dimethyl carbonate (Aldrich Corporation) was introduced to the round-bottomed flask, and then 1.1 eq (equivalent) of thionyl chloride (Aldrich Corporation), 1.15 eq of pyridine (Aldrich Corporation), 1.0 eq of 5-(hydroxymethyl)-1,2-oxathiolane-2,2-dioxide (manufactured by LG chem) were sequentially added dropwise thereto, followed by stirring the mixture at room temperature for 1 hour. Thereafter, 1.15 eq of 2,2,2-trifluoroethanol (Aldrich Corporation) and 1.15 eq of pyridine (Aldrich Corporation) were additionally slowly added dropwise in the ice bath. Thereafter, the mixture was stirred at room temperature for 1 hour, and then the residual salt was extracted using water, and an organic layer was distilled under reduced pressure to obtain an intermediate (2,2-dioxido-1,2-oxathiolan-5-yl)methyl (2,2,2-trifluoroethyl)sulfite.

Without an additional separation process, a flask containing the intermediate (2,2-dioxido-1,2-oxathiolan-5-yl) methyl (2,2,2-trifluroethyl)sulfite was placed in an ice bath, and then 1.3 eq of sodium periodate (Aldrich Corporation) and 0.01 eq of ruthenium(III) chloride (Aldrich Corporation) were introduced to a mixed solvent in which water and acetonitrile were mixed at a weight ratio of 1:1, followed by stirring the mixture in the ice bath for 1 hour.

Thereafter, t-butyl ether (Aldrich Corporation) was introduced to filter a precipitated catalyst and then an organic layer was extracted, and the catalyst was further removed using a sodium metabisulfite (Aldrich Corporation) aqueous solution, followed by performing column purification on a compound obtained after concentrating the organic layer so as to obtain a compound ((2,2-dioxido-1,2-oxathiolan-5-yl) methyl (2,2,2-trifluroethyl) sulfate) represented by Formula a below, which is a final compound (yield 27%).

[Formula a]

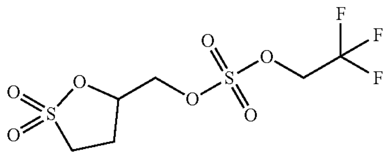

The synthesis of the compound represented by Formula a was confirmed through 1H NMR spectrum (Bruker Corporation, AVANCE NEO, 500 MHz, Acetonitrile-d).

1H NMR (Acetonitrile-d): δ 5.0 (m, 1H), δ 4.9-4.5 (m, 2H), δ 4.8 (dd, 2H), δ 3.5 (m, 2H), δ 2.8 (m, 1H), δ 2.4 (m, 1H)

Synthesis Example 2. Preparation of Compound represented by Formula b

A compound ((2,2-dioxido-1,2-oxathiolan-5-yl)methyl (2,2-difluorethyl)sulfate) represented by Formula b was obtained (yield 29%) by proceeding with a reaction in the same manner as in Synthesis Example 1 except that 2,2-difluoroethanol (Aldrich Corporation) was used instead of 2,2,2-trifluoroethanol (Aldrich Corporation).

[Formula b]

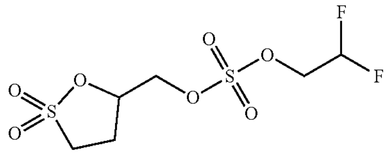

The synthesis of the compound represented by Formula b was confirmed through 1H NMR spectrum (Bruker Corporation, AVANCE NEO, 500 MHz, Acetonitrile-d).

$^{1}$H NMR (Acetonitrile-d): δ 6.1 (t, 1H), δ 5.1 (m, 1H), δ 4.9-4.4 (m, 2H), δ 4.7 (m, 2H), δ 3.4 (m, 2H), δ 2.7 (m, 1H), δ 2.3 (m, 1H)

Synthesis Example 3. Preparation of Compound Represented by Formula c

A compound (but-2-yn-1-yl((2,2-dioxido-1,2-oxathiolan-5-yl)methyl)sulfate) represented by Formula c was obtained (yield 31%) by proceeding with a reaction in the same manner as in Synthesis Example 1 except that 2-butyn-1-ol (Aldrich Corporation) was used instead of 2,2,2-trifluoroethanol (Aldrich Corporation).

[Formula c]

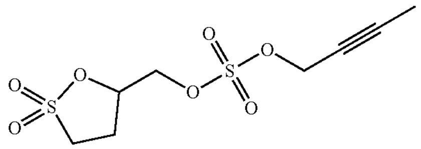

The synthesis of the compound represented by Formula c was confirmed through 1H NMR spectrum (Bruker Corporation, AVANCE NEO, 500 MHz, Acetonitrile-d).

$^{1}$H NMR (Acetonitrile-d): δ 4.9 (m, 1H), δ 4.6 (m, 2H), 4.4-4.1 (m, 2H), δ 3.4 (m, 2H), δ 2.6 (m, 1H), δ 2.4 (m, 1H), 1.8 (s, 3H)

Synthesis Example 4. Preparation of Compound Represented by Formula d

A compound ((2,2-dioxido-1,2-oxathiolan-5-yl)methyl prop-2-yn-1-yl sulfate) represented by Formula c was obtained (yield 31%) by proceeding with a reaction in the same manner as in Synthesis Example 1 except that propargyl alcohol (Aldrich Corporation) was used instead of 2,2,2-trifluoroethanol (Aldrich Corporation).

[Formula d]

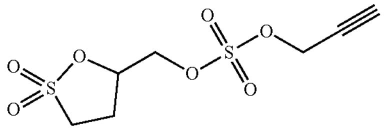

The synthesis of the compound represented by Formula d was confirmed through 1H NMR spectrum (Bruker Corporation, AVANCE NEO, 500 MHz, DMSO-d6).

1H NMR (DMSO-d6): δ 4.9 (m, 1H), δ 4.7 (dd, 2H), δ 4.3-4.1 (m, 2H), δ 3.7 (m, 1H), δ 3.5 (m, 2H), δ 2.6 (m, 1H), 2.3 (m, 1H)

Synthesis Example 5. Preparation of Compound Represented by Formula e

A compound (2-cyanoethyl ((2,2-dioxido-1,2-oxathiolan-5-yl)methyl)sulfate) represented by Formula e was obtained (yield 31%) by proceeding with a reaction in the same manner as in Synthesis Example 1 except that 3-hydroxypropanenitrile (Aldrich Corporation) was used instead of 2,2,2-trifluoroethanol (Aldrich Corporation).

[Formula e]

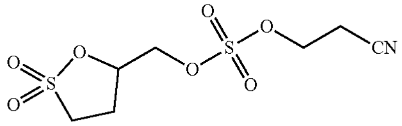

The synthesis of the compound represented by Formula e was confirmed through 1H NMR spectrum (Bruker Corporation, AVANCE NEO, 500 MHz, DMSO-d6).

1H NMR (DMSO-d6): δ 5.1 (m, 1H), δ 4.7-~4.5 (m, 4H), δ 3.5 (m, 2H), δ 3.1 (m, 2H), δ 2.9 (m, 1H), δ 2.6 (m, 1H)

Synthesis Example 6. Preparation of Compound Represented by Formula f

After a round-bottom flask was placed in an ice bath, dimethyl carbonate (Aldrich Corporation) was introduced to the round-bottomed flask, and then 1.1 eq of thionyl chloride (Aldrich Corporation), 1.15 eq of pyridine (Aldrich Corporation), 1.0 eq of 5-(hydroxymethyl)-1,2-oxathiolane-2,2-dioxide (manufactured by LG Chem) were sequentially introduced thereto, followed by stirring the mixture at room temperature for 1 hour. Thereafter, 1.15 eq of 3-hydroxypropanenitrile and 1.15 eq of pyridine (Aldrich Corporation) were additionally added dropwise in the ice bath. Thereafter, the mixture was stirred at room temperature for 1 hour, and then the residual salt was extracted using water, and an organic layer was distilled under reduced pressure to obtain a compound (2-cyanoethyl (2,2-dioxido-1,2-oxathiolan-5-yl)methyl)sulfite) represented by Formula f below (yield 35%).

[Formula f]

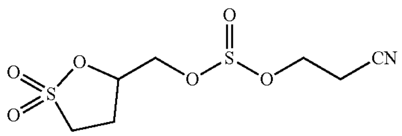

The synthesis of the compound represented by Formula f was confirmed through 1H NMR spectrum (Bruker Corporation, AVANCE NEO, 500 MHz, DMSO-d6).

$^1$H NMR (DMSO-d6): δ 5.0 (m, 1H), δ 4.4-~4.2 (m, 4H), δ 3.4 (m, 2H), δ 3.0 (m, 2H), δ 2.8 (m, 1H), δ 2.6 (m, 1H)

Examples and Comparative Examples

Example 1

(Preparation of Non-Aqueous Electrolyte Solution)

To 99 g of an organic solvent in which 1 M of $LiPF_6$ is dissolved (ethylene carbonate (EC):ethyl methyl carbonate (EMC)=3:7 volume ratio), 1 g of the compound represented by Formula a above was added to prepare a non-aqueous electrolyte solution (see Table 1 below).

(Manufacturing of Secondary Battery)

A positive electrode active material ($LiNi_{0.8}Co_{0.1}Mn_{0.1}O_2$):a conductive material (carbon black):a binder (polyvinylidene fluoride) were added at a weight ratio of 97.5:1:1.5 to N-methyl-2-pyrrolidone (NMP) to prepare a positive electrode slurry (solid content 60 wt %). The positive electrode slurry was applied on one surface of a positive electrode current collector (an Al thin film) having a thickness of 15 μm, and then dried and roll-pressed to manufacture a positive electrode.

A negative electrode active material (graphite):a conductive material (carbon black):a binder (polyvinylidene fluoride) were added at a weight ratio of 96:0.5:3.5 to distilled water to prepare a negative electrode slurry (solid content 50 wt %). The negative electrode slurry was applied on one surface of a negative electrode current collector (a Cu thin film) having a thickness of 8 μm, and then dried and roll-pressed to manufacture a negative electrode.

A porous polypropylene separator was interposed between the positive electrode and the negative electrode in a dry room to manufacture an electrode assembly, and the electrode assembly was put into a battery case, followed by injecting the non-aqueous electrolyte solution and then sealing the battery case to manufacture a pouch-type lithium secondary battery (battery capacity: 6.24 mAh).

Example 2

A lithium secondary battery was manufactured in the same manner as in Example 1 except that, as the non-aqueous electrolyte solution, a non-aqueous electrolyte solution prepared by adding the compound represented by Formula b prepared in Synthesis Example 2, instead of the compound represented by Formula a prepared in Synthesis Example 1, was used (see Table 1 below).

Example 3

A lithium secondary battery was manufactured in the same manner as in Example 1 except that a non-aqueous electrolyte solution prepared by adding 0.5 g of the compound represented by Formula a above to 99.5 g of an organic solvent in which 1 M of $LiPF_6$ is dissolved (ethylene carbonate (EC):ethyl methyl carbonate (EMC)=3:7 volume ratio) was used (see Table 1 below).

Example 4

A lithium secondary battery was manufactured in the same manner as in Example 1 except that, as the non-aqueous electrolyte solution, a non-aqueous electrolyte solution prepared by adding the compound represented by Formula c prepared in Synthesis Example 3, instead of the compound represented by Formula a prepared in Synthesis Example 1, was used (see Table 1 below).

Example 5

A lithium secondary battery was manufactured in the same manner as in Example 1 except that, as the non-aqueous electrolyte solution, a non-aqueous electrolyte solution prepared by adding the compound represented by Formula d prepared in Synthesis Example 4, instead of the compound represented by Formula a prepared in Synthesis Example 1, was used (see Table 1 below).

Example 6

A lithium secondary battery was manufactured in the same manner as in Example 1 except that, as the non-aqueous electrolyte solution, a non-aqueous electrolyte solution prepared by adding the compound represented by Formula e prepared in Synthesis Example 5, instead of the compound represented by Formula a prepared in Synthesis Example 1, was used (see Table 1 below).

Example 7

A lithium secondary battery was manufactured in the same manner as in Example 1 except that, as the non-aqueous electrolyte solution, a non-aqueous electrolyte solution prepared by adding the compound represented by Formula f prepared in Synthesis Example 6, instead of the compound represented by Formula a prepared in Synthesis Example 1, was used (see Table 1 below).

Comparative Example 1

A lithium secondary battery was manufactured in the same manner as in Example 1 except that, as the non-aqueous electrolyte solution, an organic solvent in which 1 M of $LiPF_6$ is dissolved (ethylene carbonate (EC):ethyl methyl carbonate (EMC)=3:7 volume ratio) was used instead of the non-aqueous electrolyte solution of Example 1 (see Table 1 below).

Comparative Example 2

A lithium secondary battery was manufactured in the same manner as in Example 1 except that, as the non-aqueous electrolyte solution, a non-aqueous electrolyte solution prepared by adding 1 g of 1,3-Propane sultone to 99 g of an organic solvent in which 1 M of $LiPF_6$ is dissolved (ethylene carbonate (EC):ethyl methyl carbonate (EMC)=3:7 volume ratio) was used (see Table 1 below).

TABLE 1

| | Lithium salt | Organic solvent Compositions | Organic solvent Addition amount (g) | Additive Type | Additive Addition amount (g) |
|---|---|---|---|---|---|
| Example 1 | 1.0 $LiPF_6$ | EC:EMC = 3:7 volume ratio | 99 | Compound represented by Formula a | 1 |
| Example 2 | | | 99 | Compound represented by Formula b | 1 |
| Example 3 | | | 99.5 | Compound represented by Formula a | 0.5 |
| Example 4 | | | 99 | Compound represented by Formula c | 1 |
| Example 5 | | | 99 | Compound represented by Formula d | 1 |
| Example 6 | | | 99 | Compound represented by Formula e | 1 |
| Example 7 | | | 99 | Compound represented by Formula f | 1 |
| Comparative Example 1 | | | 100 | — | 0 |
| Comparative Example 2 | | | 99 | 1,3-propane sultone | 1 |

Experimental Examples

Experimental Example 1: Evaluation of High-Temperature (60° C.) Storage Properties The volume change rate and resistance increase rate after high-temperature storage were calculated in the following manner.

(1) Volume Change Rate (%) after High-Temperature Storage

The secondary battery manufactured in each of Examples 1 to 7 and Comparative Examples 1 and 2 was activated by 0.1 C constant current (CC). Thereafter, the secondary battery was charged to 4.2 V with 0.33 C constant current under the condition of constant current-constant voltage (CC-CV) charge using a PESC05-0.5 charger/discharger (Manufacturer: PNE solution Co., Ltd) at 25° C., and then 0.05 C current cut was performed thereon, followed by discharging the secondary battery to 2.5 V with 0.33 C under the condition of CC. The above charging and discharging was set to 1 cycle, and 2 cycles were performed. Thereafter, the secondary battery was fully charged with 0.33 C/4.2 V constant current-constant voltage, and then SOC was adjusted to SOC 50%, followed by discharging the second battery with 2.5 C for 10 seconds to calculate an initial resistance through the difference between a voltage before the discharge and a voltage after the 10-second discharge. Next, the secondary battery was discharged to 2.5 V with 0.33 C constant current. Thereafter, degassing was performed, and using TWD-150DM equipment of Two-pls Corporation, the lithium secondary battery which had been subjected to initial charging/discharging was put into a bow filled with water at room temperature to measure an initial volume. Then, the lithium secondary battery was fully charged with 0.33 C/4.2 V constant current-constant voltage, and stored at 60° C. for 4 weeks (SOC 100%), and then using TWD-150DM equipment of Two-pls Corporation, the lithium secondary battery was put into a bow filled with water at room temperature to measure a volume after the high-temperature storage.

The initial volume and the volume after the high-temperature storage which were measured as described above were substituted into the following equation (1) to calculate a volume change rate (%) after the high-temperature storage, and the results are shown in Table 2 below.

$$\text{Volume change rate (\%) after hight-temperature storage} = \{(\text{Volume after high-temperature storage} - \text{Initial volume})/(\text{Initial volume})\} \times 100 \qquad \text{Equation (1)}$$

(2) Resistance Increase Rate (%) after High-Temperature Storage

The secondary battery manufactured in each of Examples 1 to 7 and Comparative Examples 1 and 2 was activated by 0.1 C constant current (CC). Thereafter, the secondary battery was charged to 4.2 V with 0.33 C constant current under the condition of constant current-constant voltage (CC-CV) charge using a PESC05-0.5 charger/discharger (Manufacturer: PNE solution Co., Ltd) at 25° C., and then 0.05 C current cut was performed thereon, followed by discharging the secondary battery to 2.5 V with 0.33 C under the condition of CC. The above charging and discharging was set to 1 cycle, and 2 cycles were performed. Thereafter, the secondary battery was fully charged with 0.33 C/4.2 V constant current-constant voltage, and then SOC was adjusted to SOC 50%, followed by discharging the second battery with 2.5 C for 10 seconds to calculate an initial resistance through the difference between a voltage before the discharge and a voltage after the 10-second discharge. Next, the secondary battery was discharged to 2.5 V with 0.33 C constant current. Thereafter, degassing was performed, and the secondary battery was charged to 4.2 V, stored (SOC 100%) at 60° C. for 4 weeks, and then discharged again at SOC 50% with 2.5 C for 10 seconds to calculate resistance after the high-temperature storage.

The initial volume and the volume after the high-temperature storage which were measured as described above were substituted into the following equation (2) to calculate a resistance increase rate (%) after the high-temperature storage, and the results are shown in Table 2 below.

$$\text{Resistance increase rate (\%) after high-temperature storage} = \{(\text{Resistance after high-temperature storage} - \text{Initial resistance})/(\text{Initial resistance})\}\times 100 \quad \text{Equation (2)}$$

TABLE 2

| | Volume change rate after high-temperature storage (%) | Resistance increase rate after high-temperature storage (%) |
|---|---|---|
| Example 1 | 9 | 8 |
| Example 2 | 12 | 10 |
| Example 3 | 11 | 9 |
| Example 4 | 17 | 15 |
| Example 5 | 12 | 14 |
| Example 6 | 8 | 7 |
| Example 7 | 13 | 10 |
| Comparative Example 1 | 37 | 45 |
| Comparative Example 2 | 25 | 40 |

Experimental Example 2: Evaluation of Cycle Properties

The secondary battery manufactured in each of Examples 1 to 7 and Comparative Examples 1 and 2 was activated by 0.1 C constant current (CC). Thereafter, the secondary battery was charged to 4.2 V with 0.33 C constant current under the condition of constant current-constant voltage (CC-CV) charge using a PESC05-0.5 charger/discharger (Manufacturer: PNE solution Co., Ltd) at 25° C., and then 0.05 C current cut was performed thereon, followed by discharging the secondary battery to 2.5 V with 0.33 C under the condition of CC. The above charging and discharging was set to 1 cycle, and 2 cycles were performed. Thereafter, the secondary battery was fully charged with 0.33 C/4.2 V constant current-constant voltage, and then SOC was adjusted to SOC 50%, followed by discharging the second battery with 2.5 C for 10 seconds to calculate an initial resistance through the difference between a voltage before the discharge and a voltage after the 10-second discharge. Next, the secondary battery was discharged to 2.5 V with 0.33 C constant current.

Thereafter, degassing was performed, and under the condition of CC-CV charge at 45° C., the secondary battery was charged to 4.2 V with a constant current of 0.33 C, followed by a 0.05 C current cut, and then discharged to 2.5 V with 0.33 C under the condition of CC. The above charging and discharging was set to 1 cycle, and 100 cycles were performed. At this time, the discharge capacity (initial discharge capacity) after the first cycle and the discharge capacity after the 100-th cycle were measured using a PESC05-0.5 charger and discharger (Manufacturer: PNE solution Co., Ltd, 5 V, 50 OmA), and the discharge capacity retention rate after 100 cycles was calculated using the following equation (3). The results are shown in Table 3 below.

$$\text{Discharge capacity retention rate after 100 cycles (\%)} = \{(\text{Discharge capacity after 100 cycles})/\text{Initial discharge capacity}\}\times 100 \quad \text{Equation (3)}$$

Meanwhile, after performing 100 cycles, the secondary battery was discharged at SOC 50% with 2.5 C for 10 seconds, and the resistance after 100 cycles was calculated through the difference between a voltage before the discharge and a voltage after the 10-second discharge. The initial resistance and the resistance after the 100 cycles which were calculated as described above were substituted into the following (4) to calculate a resistance increase rate (%) after the 100 cycles, and the results are shown in Table 3 below.

$$\text{Resistance increase rate (\%) after 100 cycles} = \{(\text{Resitance after 100 cycles}/(\text{Initial resitance})\}\times 100 \quad \text{Equation (4)}$$

TABLE 3

| | Discharge capacity retention rate after 100 cycles (%) | Resistance increase rate after 100 cycles (%) |
|---|---|---|
| Example 1 | 93 | 10 |
| Example 2 | 91 | 12 |
| Example 3 | 88 | 15 |
| Example 4 | 89 | 17 |
| Example 5 | 91 | 16 |
| Example 6 | 94 | 9.5 |
| Example 7 | 92 | 14 |
| Comparative Example 1 | 78 | 40 |
| Comparative Example 2 | 85 | 24 |

Referring to Table 2 above, it can be confirmed that the secondary batteries manufactured in Examples 1 to 7 have a volume change rate and a resistance increase rate during high-temperature storage which are significantly lower than those of the secondary batteries manufactured in Comparative Examples 1 and 2. In addition, referring to Table 3, it can be confirmed that the secondary batteries manufactured in Examples 1 to 7 have a high discharge capacity retention rate and a low resistance increase rate after 100 cycles, and thus have lifespan properties which are significantly superior to those of the secondary batteries manufactured in Comparative Examples 1 and 2. These properties are due to the fact that the sultone-based compound (the compound represented by Formula I of the present invention) included in the non-aqueous electrolyte solution of Examples 1 to 7 efficiently generate a SEI layer with high stability and low resistance.

Therefore, when a compound represented by Formula I is included as an additive in a non-aqueous electrolyte solution as in the present invention, it can be seen that the flammability of the non-aqueous electrolyte solution may be lowered, and an SEI layer which is low in resistance and robust may be formed, so that a lithium secondary battery with excellent high-temperature stability and lifespan properties may be provided.

The invention claimed is:

1. A compound represented by Formula I:

[Formula I]

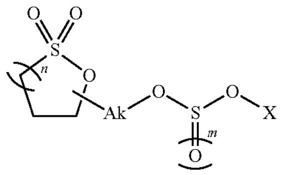

wherein, in Formula I, n and m are each independently 1 or 2,

Ak is a substituted or unsubstituted $C_1$-$C_{10}$ alkylene group, and

X is a $C_1$-$C_{10}$ alkyl group substituted with one or more halogen elements; a —Y1-C≡C-Y2 group; or a —Y1-CN group, wherein the Y1 is a direct linkage; or a substituted or unsubstituted $C_1$-$C_{10}$ alkylene group; and the Y2 is hydrogen; or a substituted or unsubstituted $C_1$-$C_{10}$ alkyl group.

2. The compound of claim 1, wherein the Ak is an unsubstituted $C_1$-$C_6$ alkylene group.

3. The compound of claim 1, wherein the X is a $C_1$-$C_6$ alkyl group substituted with one or more halogen elements.

4. The compound of claim 1, wherein the X is a —Y1'-C≡C-Y2' group, wherein the Y1' is an unsubstituted $C_1$-$C_6$ alkylene group; and the Y2' is hydrogen; or an unsubstituted $C_1$-$C_6$ alkyl group.

5. The compound of claim 1, wherein the X is a —Y1'—CN group, wherein the Y1' is an unsubstituted $C_1$-$C_6$ alkylene group.

6. The compound of claim 1, wherein the compound represented by Formula I is a compound which is a compound represented by Formula 1:

[Formula 1]

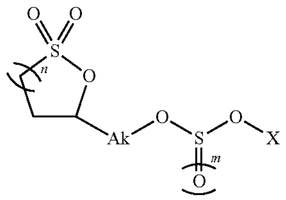

wherein in Formula 1, n, m, AK, and X are described as in Formula I.

7. The compound of claim 1, wherein the compound represented by Formula I is a compound which is any one among compounds represented by Formula a to Formula f:

[Formula a]

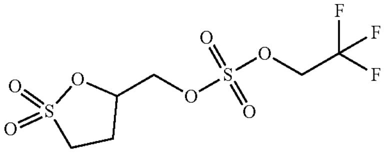

[Formula b]

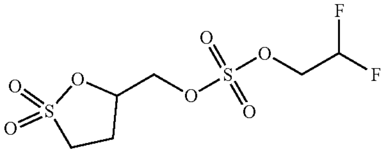

[Formula c]

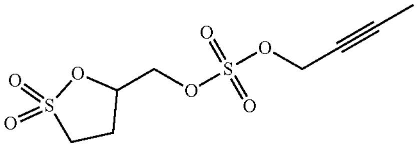

[Formula d]

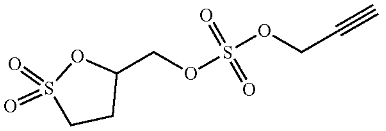

[Formula e]

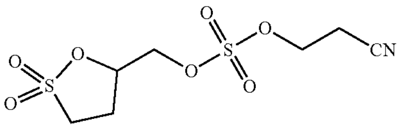

[Formula f]

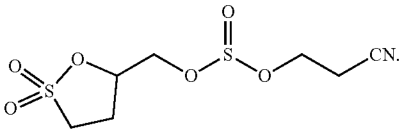

8. A non-aqueous electrolyte solution comprising an organic solvent; a lithium salt; and a compound according to claim 1.

9. The non-aqueous electrolyte solution of claim 8, wherein the compound is included in an amount of 0.01 wt % to 10 wt % based on the total weight of the non-aqueous electrolyte solution.

10. A lithium secondary battery comprising a positive electrode including a positive electrode active material, a negative electrode including a negative electrode active material, a separator interposed between the positive electrode and the negative electrode, and the non-aqueous electrolyte solution according to claim 8.

* * * * *